United States Patent [19]

De Ruiter

[11] Patent Number: Plant 6,236

[45] Date of Patent: Aug. 2, 1988

[54] MINIATURE ROSE PLANT NAMED 'RUISETO'

[75] Inventor: Gijsbert De Ruiter, Hazerswoude, Netherlands

[73] Assignee: De Ruiter's Nieuwe Rozen B.V., Hazerswoude, Netherlands

[21] Appl. No.: 887,704

[22] Filed: Jul. 21, 1986

[51] Int. Cl.[4] ..... A01H 5/00

[52] U.S. Cl. ..... Plt./10

[58] Field of Search ..... Plt. 10

*Primary Examiner*—Robert E. Bagwill

*Attorney, Agent, or Firm*—Charles W. Rummler

[57] ABSTRACT

A new variety of miniature rose characterized by a continuous and profuse production of small orange-red blooms carried on very long, strong stems; the blooms are approximately 40 millimeters in diameter; its formed flowers having many petals which tend to marginally turn under and form points. This new miniature rose variety has a free branching and vigorous growth habit producing a dwarf, compact, bushy and free blooming plant that is suitable for use as a pot plant as well as for garden decoration.

1 Drawing Sheet

BACKGROUND OF THE NEW PLANT

My new variety of rose plant is the result of breeding efforts carried on by me at Hazerswoude, Holland, with the object of producing a miniature rose suitable for production of flowering pot plants as well as being useful for garden decoration. This plant originated as a seedling derived by my crossing of an unnamed seedling with the variety 'Ruiredro'. The profusion and beauty of the flowers of this new plant and its very fine growth habit led me to propagate it by budding for observation and test purposes, which was so satisfactory that I directed that propagation of this plant by budding and cuttings be continued through several successive generations, which showed that the novel characteristics of this plant would hold true from generation to generation and appeared to be firmly fixed. Commercial propagation of this plant, by budding, is now being carried on in Holland.

DESCRIPTION OF THE DRAWING

My new variety of rose plant is illustrated by the accompanying photographic drawing, which shows the vegetative growth and flowering of this variety and is depicted in color as true to that specified herein as is reasonably possible to make in a color illustration of this character. The specimens illustrated were grown in greenhouse in July 1985 at Hazerswoude with three plants in one pot.

DESCRIPTION OF THE NEW PLANT

The following combination of characteristics is observed in this new variety:

(a) Readily propagated and grown on its own roots by cuttings;

(b) Exhibits a well balanced, compact and vigorous growth habit which is extremely floriferous;

(c) Blooms carried in clusters as well as one per stem;

(d) Exhibits an excellent aptitude for greenhouse forcing as a flowering pot plant and also has a very good comportment when used as an outdoor garden plant;

(e) Bloom color is uniform throughout the flower and in general orange-red.

The following is a detailed description of this new rose plant based upon observations of plants grown in a greenhouse in Hazerswoude, Holland, in early December.

Throughout this specification, color identification is based upon The R.H.S. Colour Chart published by The Royal Horticultural Society of London, England.

THE PLANT

Origin: Seedling.

Parentage:

*Seed parent.*—An unpatented rose plant of an unnamed variety.

*Pollen parent.*—'Ruiredro'.

Classification:

*Botani.*—Rose Hybrid.

*Commercial.*—Miniature Rose.

Form: Bush.

Growth habit: Vigorous, upright and much branched.

Height: About 20 to 25 cm.

Growth Rate: Fast.

Canes:

*Length.*—About 9 to 11 cm. (measured from base of the stem to flower cluster).

*Diameter.*—About 1.5 mm. to 2.3 mm.

*Color.*—Green, 137B/C.

Branching: Moderate to good.

Foliage:

*Quantity.*—Normal.

*Number of leaves.*—5 or 6.

*Shape of leaf.*—Odd pinnate.

*Size of leaf.*—About 50 to 56 mm. long and 34 to 42 mm. wide.

*Color.*—New foliage, Yellow-Green, 147A. Old foliage, Green, 137A.

*Leaflets.*—Shape: Elliptic. Number: 3 or 5. Margins: Serrated. Texture: Firm. Serration: Double, small. Shape base of terminal leaflet: Obtuse. Petioles: Color: Green under side with prickles. Stipules: Small, slightly bearded.

Thorns:

*Quantity.*—On main canes from base, few. On laterals from main canes, few.

*Form.*—Concave, thin.

*Color when young.*—Pale yellow.

THE BUD

Form: Ovate.

Size:

*When petals start to unfurl.*—Diameter — 9.5 to 10.00 mm. Length — 11.5 to 12.5 mm.

Color: When sepals first divide, Red, 45D.

Sepals:

*Color.*—Green, 143A. Extensions absent in two, medium in three.

Receptacle:

*Color.*—Green, 143C.

*Shape.*—Pitcher or pear shaped.

*Size.*—Small. Length — About 7 mm. Width — About 10 mm.

*Surface.*—Smooth, dull.

*Peduncle.*—Length: Medium; About 26 to 37 mm. Color: Yellow-Green, 144A–146B.

THE FLOWER

Blooming habit: Continuous an abundant.

Borne: Singly and in clusters of two or three.

Size: Average open size, about 40 mm.

Form:

*Upper part.*—Convex.

*Under part.*—Flat.

Stem: Medium.

Petalage:

*Number of petals.*—30 to 35.

*Arrangement.*—Irregular — imbricate.

*Form.*—Medium undulation; reflexing absent young, strong when old.

*Shape.*—Elliptic with dent at center of outer margin.

*Texture.*—Medium thick, firm.

*Color.*—Upper side of petals: Marginal zone — Red, 44B. Middle zone — Red, 44B. Basal zone — Red, 41B. Basal spot — Yellow-Green, 154C. Reverse side: Marginal zone — Red, 46C. Middle zone — Red 45C. Basal zone — Red, 43C. Basal spot — Yellow-Green, 154C.

Persistence: The petals hand on and dry.

Lasting quality: On the plant, long.

REPRODUCTIVE ORGANS

Stamens:

*Number.*—35 to 40.

*Arrangement.*—Regular around the styles.

*Anthers.*—Size: Small. Color: Yellow Orange, 15A.

*Filaments.*—Length: 2 to 3 mm. Color: Green-Yellow, 1D.

*Pollen.*—Color: Greyed Orange, 167C.

Pistils:

*Number.*—15 to 20.

*Styles.*—Length: 5 to 6 mm. Color: Green, 142C.

*Stigmas.*—Color: Orange Red, 31D.

*Ovaries.*—Normal.

I claim:

1. A new and distinct variety of rose plant of the miniature class, substantially as herein shown and described, characterized by being a dwarf, compact, free blooming plant, having blooms with petals of heavy substance and of orange-red color approximately 40 millimeters in diameter, and being suitable for use as a pot plant as well as for garden decoration.

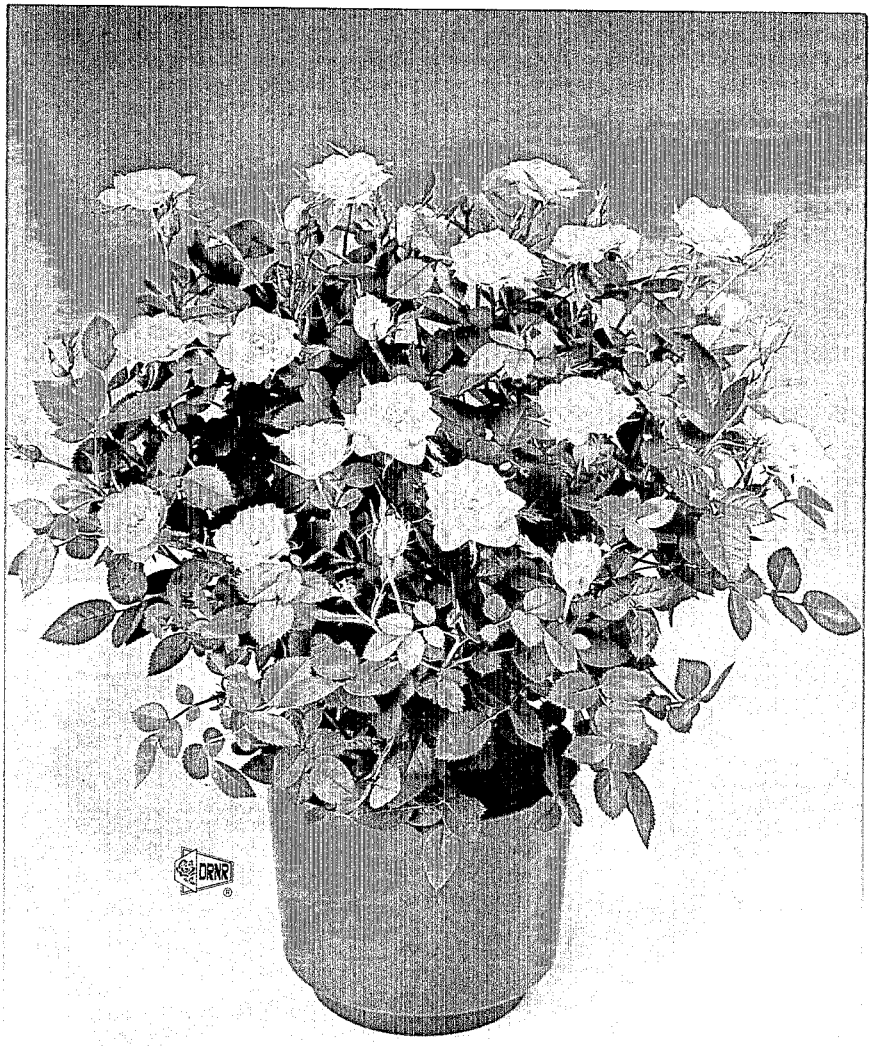

* * * * *